(12) United States Patent
Onishi

(10) Patent No.: US 9,829,422 B2
(45) Date of Patent: Nov. 28, 2017

(54) CONCENTRATION METER AND ENDOSCOPE REPROCESSOR

(71) Applicant: OLYMPUS CORPORATION, Tokyo (JP)

(72) Inventor: Hideto Onishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/368,923

(22) Filed: Dec. 5, 2016

(65) Prior Publication Data

US 2017/0082529 A1 Mar. 23, 2017

Related U.S. Application Data

(63) Continuation of application No. PCT/JP2016/060421, filed on Mar. 30, 2016.

(30) Foreign Application Priority Data

Jun. 4, 2015 (JP) .................................. 2015-114143

(51) Int. Cl.
| | |
|---|---|
| *G01N 15/06* | (2006.01) |
| *A61B 1/015* | (2006.01) |
| *A61B 1/12* | (2006.01) |
| *A61L 2/18* | (2006.01) |
| *G01N 27/26* | (2006.01) |

(Continued)

(52) U.S. Cl.
CPC ......... *G01N 15/0618* (2013.01); *A61B 1/015* (2013.01); *A61B 1/12* (2013.01); *A61L 2/18* (2013.01); *G01N 15/0656* (2013.01); *G01N 27/26* (2013.01); *G01N 27/333* (2013.01); *G01N 27/404* (2013.01); *G01N 27/416* (2013.01)

(58) Field of Classification Search
None
See application file for complete search history.

(56) References Cited

U.S. PATENT DOCUMENTS 8,012,770 B2 * 9/2011 Siciliano ............... B01L 3/5023
422/401

FOREIGN PATENT DOCUMENTS

| JP | 56-43554 A | 4/1981 |
|---|---|---|
| JP | 63-38053 U | 3/1988 |

(Continued)

*Primary Examiner* — Daniel S Larkin
(74) *Attorney, Agent, or Firm* — Scully, Scott, Murphy & Presser, P.C.

(57) ABSTRACT

A concentration meter invention includes a housing having a cavity, an electrode accommodated in the cavity, a permeation membrane that has a measurement surface that contacts a measurement target, a releasing surface that releases the measurement target that enters from the measurement surface into the cavity, and a plurality of holes that open to the measurement surface and the releasing surface, and are for the measurement target to enter, and seals the cavity, an internal liquid that is sealed in the cavity, and contacts the electrode and the permeation membrane, an adjustment section that applies a mechanical load to the permeation membrane so that opening areas of the holes in at least the measurement surface reversibly increase or decrease, and a control section that is connected to the adjustment section, and controls change of strength of the mechanical load that is applied to the permeation membrane.

8 Claims, 13 Drawing Sheets

(51) Int. Cl.
   *G01N 27/333*   (2006.01)
   *G01N 27/404*   (2006.01)
   *G01N 27/416*   (2006.01)

(56) References Cited

FOREIGN PATENT DOCUMENTS

| | | |
|---|---|---|
| JP | 2006-234508 A | 9/2006 |
| JP | 2010-57792 A | 3/2010 |
| JP | 2013-64702 A | 4/2013 |
| JP | 5826982 B1 | 10/2015 |
| JP | 5893817 B1 | 3/2016 |
| WO | WO 2016/035377 A1 | 3/2016 |

* cited by examiner

CONCENTRATION METER AND ENDOSCOPE REPROCESSOR

CROSS REFERENCE TO RELATED APPLICATION

This application is a continuation application of PCT/JP2016/060421 filed on Mar. 30, 2016 and claims benefit of Japanese Application No. 2015-114143 filed in Japan on Jun. 4, 2015, the entire contents of which are incorporated herein by this reference.

BACKGROUND OF THE INVENTION

1. Field of the Invention

The present invention relates to a concentration meter including a permeation membrane and an endoscope reprocessor.

2. Description of the Related Art

As a concentration meter that measures a concentration of a measurement target in a liquid, there is known a concentration meter with a mode including a permeation membrane that allows a measurement target in a liquid to permeate through, as disclosed in Japanese Patent Application Laid-Open Publication No. 2006-234508, for example. When the concentration of a measurement target in a liquid is measured by using a concentration meter including a permeation membrane, a measurement surface that is a surface of the permeation membrane is brought into contact with the liquid.

SUMMARY OF THE INVENTION

A concentration meter according to one aspect of the present invention includes a housing having a cavity, an electrode accommodated in the cavity, a permeation membrane that has a measurement surface that contacts a measurement target, a releasing surface that releases the measurement target that enters from the measurement surface into the cavity, and a plurality of holes that open to the measurement surface and the releasing surface, and are for the measurement target to enter, and seals the cavity, an internal liquid that is sealed in the cavity, and contacts the electrode and the permeation membrane, a main body connection section for electrically connecting the electrode to an endoscope reprocessor main body, an adjustment section that applies a mechanical load to the permeation membrane so that opening areas of the holes in at least the measurement surface reversibly increase or decrease, and a control section that is connected to the adjustment section, and controls change of strength of the mechanical load that is applied to the permeation membrane, or presence or absence of the mechanical load that is applied to the permeation membrane.

An endoscope reprocessor according to one aspect of the present invention includes the concentration meter, a medicinal solution tank that stores a medicinal solution including the measurement target, a holding portion that holds the housing so that the permeation membrane is immersed in the medicinal solution in the medicinal solution tank, and an electric contact point that is connected to the main body connection section.

DETAILED DESCRIPTION OF THE PREFERRED EMBODIMENT(S)

Figure 1:
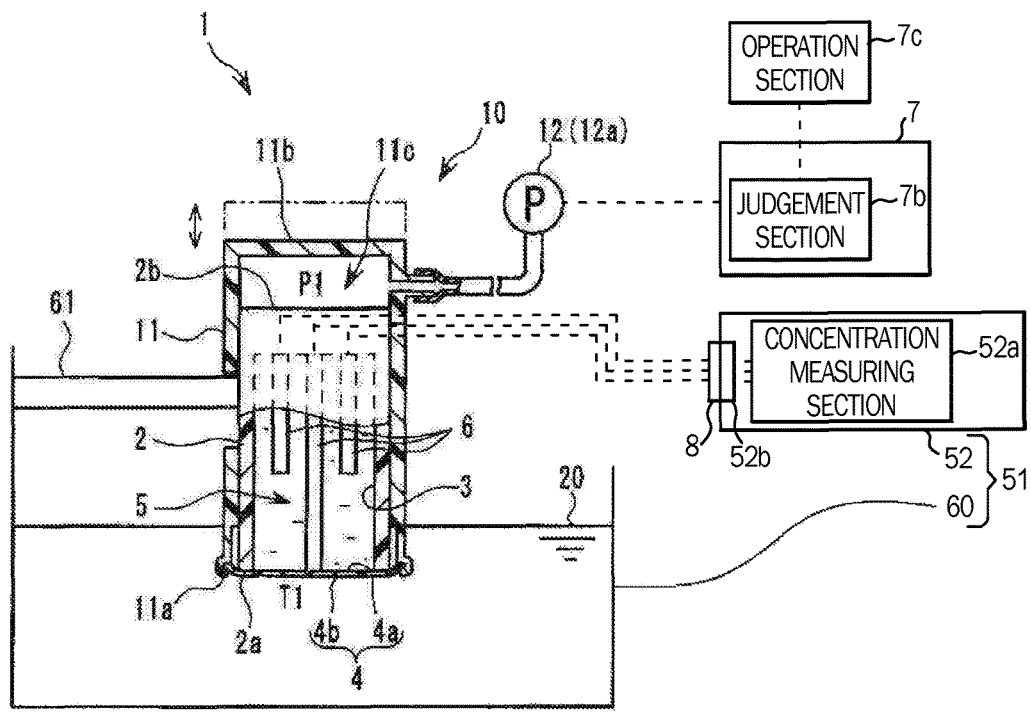
FIG. 1 is a view illustrating a configuration of a concentration meter of a first embodiment.

Hereinafter, preferable modes of the present invention will be described with reference to the drawings. Note that in the respective drawings for use in the following explanation, in order to make respective components have such sizes as to be recognizable on the drawings, a scale is caused to differ for each of the components, and the present invention is not limited to only the numbers and quantities of the components, shapes of the components, ratios of the sizes of the components, and relative positional relations of the respective components which are illustrated in the drawings.

First Embodiment

Hereinafter, one example of an embodiment of the present invention will be described. A concentration meter 1 illustrated in FIG. 1 is a device that measures a concentration of a measurement target that is present in a liquid 20.

The concentration meter 1 includes a control section 7, a housing 2, a permeation membrane 4, an internal liquid 5, an electrode 6, an adjustment section 10, and a main body connection section 8. The concentration meter 1 of the present embodiment is set to an endoscope reprocessor main body 51. The concentration meter 1 that is set to the endoscope reprocessor main body 51 measures a concentration of a measurement target that is present in the liquid 20 which is stored in a medicinal solution tank 60. A configuration of the endoscope reprocessor will be described later.

The control section 7 is configured by including an arithmetic unit (CPU), a storage device (RAM), an auxiliary storage device, an input/output device and an electric power control device and the like, and has a configuration controlling operations of the respective parts which configure the concentration meter 1 based on a predetermined program. Operations of respective components included in the concentration meter 1 in the following explanation are controlled by the control section 7 even when no explanation is specially made.

The housing 2 has a cavity 3 in a concave shape. In the present embodiment, as an example, the housing 2 having a cylindrical shape, a distal end portion 2a at one side is open along a center axis, and a proximal end portion 2b at the other side is closed. That is, the cavity 3 of the housing 2 of the present embodiment is open in the distal end portion 2a of the housing 2.

In an interior of the cavity 3, the internal liquid 5 and a plurality of electrodes 6 are placed. The permeation membrane 4 covers the cavity 3 that is provided in the housing 2, and seals an opening portion of the cavity 3 so that the internal liquid 5 does not leak from an inside of the cavity 3.

The plurality of electrodes 6 that are placed in the cavity 3 are separated from one another, and are immersed in the internal liquid 5. That is, the internal liquid 5 is in contact with a releasing surface 4a of the permeation membrane 4 and the electrodes 6, in the cavity 3.

The electrode 6 is electrically connected with the main body connection section 8. The main body connection section 8 is for contacting an electric contact point 52b of an endoscope reprocessor main body 51 when the concentration meter 1 is set to the endoscope reprocessor main body 51. The electric contact point 52b is electrically connected to a concentration measuring section 52a that is included in the endoscope reprocessor main body 51. That is, the main body connection section 8 electrically connects the electrodes 6 to the endoscope reprocessor main body 51.

Hereinafter, in a surface of the permeation membrane 4, a surface contacting the internal liquid 5 will be referred to as the releasing surface 4a, and a surface at an opposite side from the releasing surface 4a will be referred to as a measurement surface 4b. That is, the releasing surface 4a of the permeation membrane 4 is a surface that faces an inside of the cavity 3.

In the present embodiment, as one example, the permeation membrane 4 is held in a state where a tensile force is applied to the permeation membrane 4 by the adjustment section 10 that will be described later. The permeation membrane 4 is an elastic body, and elastically deforms in accordance with a change of the tensile force which is applied. The permeation membrane 4 seals the cavity 3 by the releasing surface 4a abutting on the distal end portion 2a of the housing 2 in a state where a predetermined tensile force is applied to the permeation membrane 4. That is, the releasing surface 4a of the permeation membrane 4 adheres closely to a periphery of an opening of the cavity 3 with a pressure of a predetermined value or more, and eliminates a gap between the distal end portion 2a of the housing 2 and the releasing surface 4a. Note that a member that enhances sealing performance such as an O-shaped ring may be sandwiched between the distal end portion 2a of the housing 2, and the releasing surface 4a of the permeation membrane 4.

The permeation membrane 4 is immersed in the liquid 20 which is stored in the medicinal solution tank 60 in the state where the concentration meter 1 is set to the endoscope reprocessor main body 51. More specifically, the housing 2 is held in the medicinal solution tank 60 by a holding portion 61. The housing 2 is held by the holding portion 61, whereby the measurement surface 4b of the permeation membrane 4 is held at a position where the measurement surface 4b is immersed in the liquid in the medicinal solution tank 60.

Figure 2:
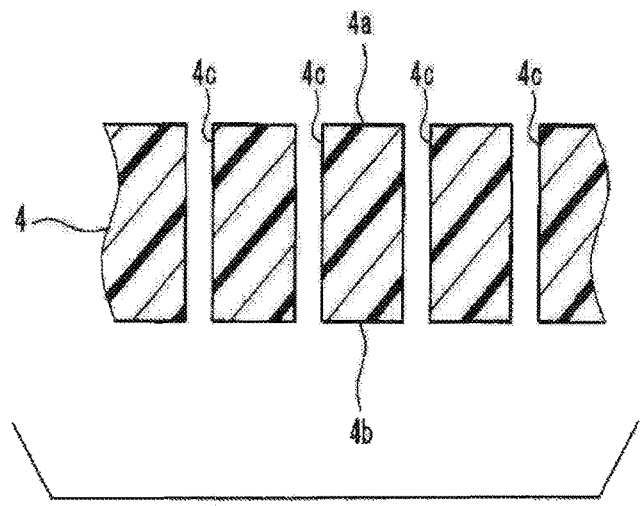
FIG. 2 is a view illustrating a section of a permeation membrane of the first embodiment by enlarging the section of the permeation membrane.
Figure 3:
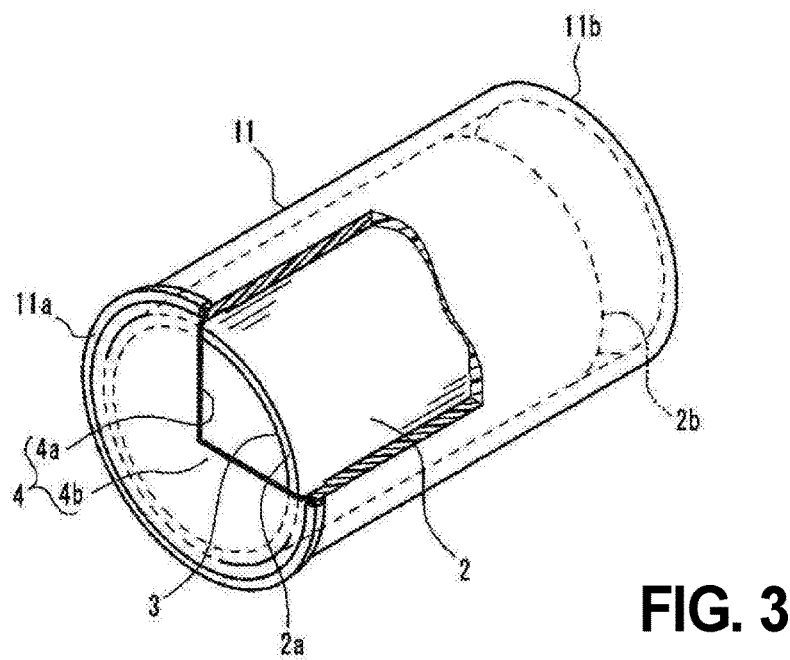
FIG. 3 is a perspective view of a housing and an outer frame of the first embodiment.

The measurement surface 4b of the permeation membrane 4 is a surface that contacts the liquid 20. As illustrated in a sectional view in FIG. 2, the permeation membrane 4 has a plurality of holes 4c that allow a measurement target to permeate through, and do not allow the liquid 20 and the internal liquid 5 to permeate through. The individual holes 4c open in the measurement surface 4b and the releasing surface 4a. Note that FIG. 2 is a schematic view, and a shape and disposition of the hole 4c are not limited to FIG. 2.

The permeation membrane 4 allows the measurement target to permeate through in accordance with a permeation pressure that is generated by a difference between a concentration of the measurement target in the liquid 20 and a concentration of the measurement target in the internal liquid 5. For example, when the concentration of the measurement target in the liquid 20 that contacts the measurement surface 4b is higher than the concentration of the measurement target in the internal liquid 5, the measurement target in the liquid 20 enters into an opening at the measurement surface 4b side of the hole 4c of the permeation membrane 4, and is released into the internal liquid 5 from an opening at the releasing surface 4a side of the hole 4c. That is, the concentration of the measurement target in the internal liquid 5 changes in accordance with the concentration of the measurement target in the liquid 20 that contacts the measurement surface 4b of the permeation membrane 4.

The concentration measuring section 52a measures a change of a potential difference that occurs among the plurality of electrodes 6 that are immersed in the internal liquid 5, or a change of a value of a current that flows among the plurality of electrodes 6, and measures the concentration of the liquid 20 that contacts the measurement surface 4b based on the measurement value. A principle and a configuration of the concentration measurement in the concentration meter 1 like this are well known, and therefore detailed explanation will be omitted.

Note that the control section 7 of the concentration meter 1 may have a configuration measuring the change of the potential difference that occurs among the plurality of electrodes 6, or the change of the value of the current flowing among the plurality of electrodes 6, and measuring the concentration of the liquid 20 that contacts the measurement surface 4b based on the measurement value. In this case, information on the measurement of the concentration by the concentration meter 1 is inputted to the concentration measuring section 52a via the main body connection section 8.

The adjustment section 10 applies mechanical load to the permeation membrane 4 so that any one of a thickness of the permeation membrane 4, an opening area of the hole 4c of the permeation membrane 4, an opening shape of the hole 4c of the permeation membrane 4 and a combination of the thickness, the opening area, and the opening shape changes reversibly.

In the present embodiment, as one example, the mechanical load that is applied to the permeation membrane 4 by the adjustment section 10 is a tensile force. The adjustment section 10 can change the tensile force that is applied to the permeation membrane 4. The adjustment section 10 of the present embodiment includes an outer frame 11 and an actuator 12.

The outer frame 11 holds the permeation membrane 4, is disposed at an outer circumference of the housing 2, and moves to advance and retreat along the housing 2. A direction in which the outer frame 11 moves to advance and retreat is a direction from the distal end portion 2a of the housing 2 to the proximal end portion 2b, and an opposite direction to the direction.

More specifically, the outer frame 11 is a member having a cylindrical shape that is slidably fitted onto the outer circumference of the housing 2. In the outer frame 11, a distal end portion 11a at one side is open along a center axis, and a proximal end portion 11b at the other side is closed. In the outer frame 11, the distal end portion 11a faces the same direction as the distal end portion 2a of the housing 2 in a state where the housing 2 is fitted to an inside.

In the state where the housing 2 is fitted to the inside of the outer frame 11, an adjustment chamber 11c that is a space enclosed by an inner wall surface of the outer frame 11 and an outer wall surface of the proximal end portion 2b of the housing 2 is generated between the proximal end portion 11b of the outer frame 11 and the proximal end portion 2b of the housing 2. A bidirectional dimension along a center axis of the outer frame 11 of the adjustment chamber 11c changes with advancing and retreating movement of the outer frame 11 relative to the housing 2.

At the distal end portion 11a of the outer frame 11, the permeation membrane 4 is disposed in a stretched state. The permeation membrane 4 is disposed at the distal end portion 11a of the outer frame 11 in a stretched state in such a manner that the releasing surface 4a faces an inside of the outer frame 11. Inside the outer frame 11, the distal end portion 2a of the housing 2 abuts on the releasing surface 4a of the permeation membrane 4 as described above.

The actuator 12 has a mechanism that causes the outer frame 11 to move to advance and retreat relative to the housing 2. The actuator 12 is electrically connected to the control section 7, and an operation of the actuator 12 is controlled by the control section 7.

Although a configuration of the actuator 12 is not specially limited, the actuator 12 of the present embodiment includes a pump 12a that changes an air pressure or a liquid pressure in the adjustment chamber 11c. In the present embodiment, as one example, the pump 12a changes the air pressure in the adjustment chamber 11c. The air pressure in the adjustment chamber 11c is changed by the pump 12a, whereby the outer frame 11 moves to advance and retreat relative to the housing 2 in accordance with the air pressure in the adjustment chamber 11c.

For example, in the present embodiment, in a case where the air pressure in the adjustment chamber 11c is an atmospheric pressure or an air pressure P1 that is lower than the atmospheric pressure, the outer frame 11 is located in a first position that is a position that is nearest to the distal end portion 2a side in a relatively movable range to the housing 2, as illustrated in FIG. 1. A tensile force that is applied to the permeation membrane 4 in a case where the outer frame 11 is located in the first position is a first tensile force T1.

Figure 4:
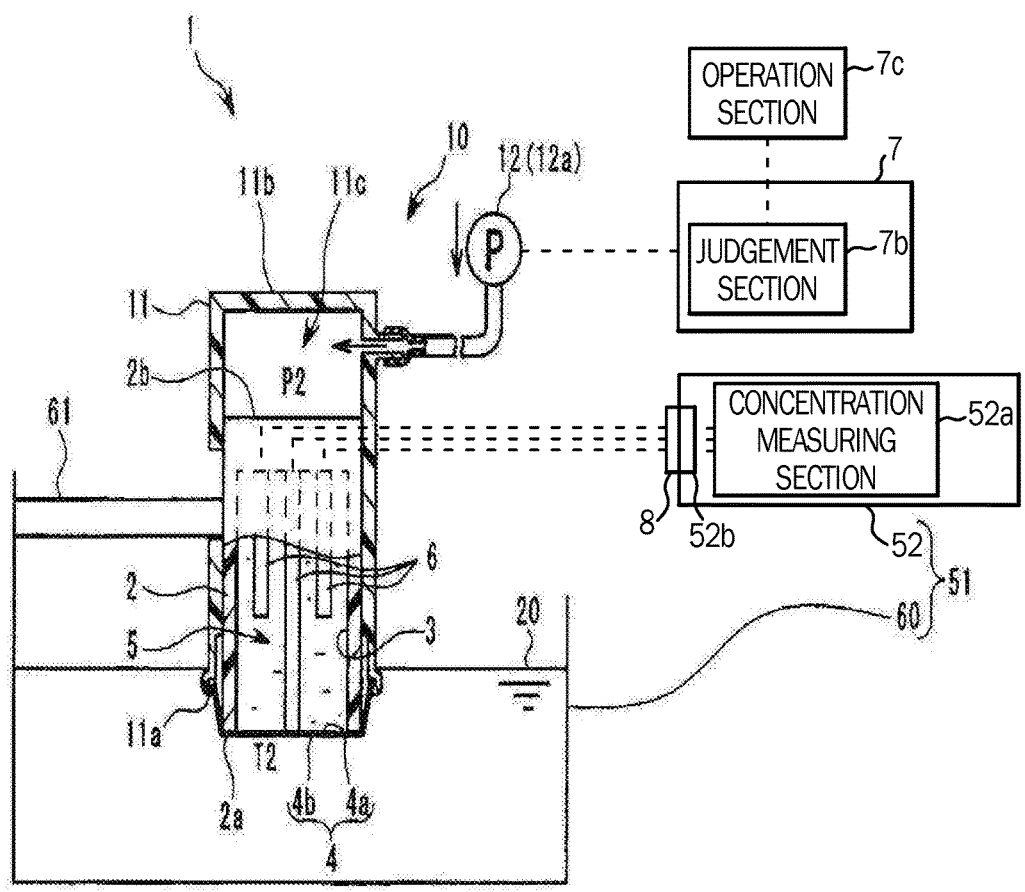
FIG. 4 is a view illustrating a state where a tensile force that is added to the permeation membrane is increased in the concentration meter of the first embodiment.

Further, for example, when the air pressure in the adjustment chamber 11c is a predetermined air pressure P2 that is higher than the atmospheric pressure, the outer frame 11 moves to a proximal end portion 2b side from the first position with respect to the housing 2, as illustrated in FIG. 4. The outer frame 11 moves to the proximal end portion 2b side from the first position with respect to the housing 2, whereby the permeation membrane 4 that is provided by being stretched at the distal end portion 11a of the outer frame 11 is pressed from an inside to an outside by the housing 2, and therefore the tensile force which is applied to the permeation membrane 4 becomes higher than the first tensile force T1. The tensile force that is applied to the permeation membrane 4 in a case where the outer frame 11 moves to the proximal end portion 2b side from the first position with respect to the housing 2 is set as a second tensile force T2. The second tensile force T2 may be a variable value or a fixed value.

Note that the actuator 12 preferably includes a pressure sensor that measures the air pressure or the liquid pressure in the adjustment chamber 11c, or a position sensor that measures a relative position of the outer frame 11 to the housing 2.

The permeation membrane 4 is an elastic body, and therefore elastically deforms in accordance with the change of the tensile force which is applied. Since in the present embodiment, the outer frame 11 and the housing 2 have cylindrical shapes, the tension force is isotropically applied to the permeation membrane 4. Accordingly, as the tensile force which is applied to the permeation membrane 4 becomes higher, a thickness of the membrane 4 becomes thinner, and the opening area of the hole 4c becomes larger.

The control section 7 includes a judgment section 7b. The judgment section 7b judges whether or not the measurement surface 4b of the permeation membrane 4 is in a wet state. A configuration of the judgment section 7b is not specially limited, but in the present embodiment, as one example, the judgment section 7b is electrically connected to an operation section 7c that is operated by a user.

The operation section 7c includes an operation member such as a push switch and a touch sensor. The judgment section 7b judges whether or not the measurement surface 4b of the permeation membrane 4 is in a wet state in accordance with an operation state of the operation section 7c by the user.

When the judgment section 7b judges that the measurement surface 4b of the permeation membrane 4 is in a wet state, for example, the control section 7 controls the adjustment section 10 to set the tensile force which is applied to the permeation membrane 4 at the first tensile force T1. That is, the control section 7 controls the actuator 12 in the adjustment section 10, and disposes the outer frame 11 in the first position.

Further, when the judgment section 7b judges that the measurement surface 4b of the permeation membrane 4 is not in a wet state, for example, the control section 7 controls the adjustment section 10 to set the tensile force which is applied to the permeation membrane 4 at the second tensile force T2 which is higher than the first tensile force T1. That is, the control section 7 controls the actuator 12 in the adjustment section 10, and disposes the outer frame 11 in the position which is at the proximal end portion 2a side from the first position.

As described above, the concentration meter 1 of the present embodiment includes the housing 2 having the cavity 3, the permeation membrane 4 that seals the cavity 3, the internal liquid 5 and the electrodes 6 that are enclosed in the cavity 3, and the adjustment section 10 that holds the permeation membrane 4 and changes the mechanical addition which is applied to the permeation membrane 4. More specifically, the adjustment section 10 of the present embodiment changes the tensile force that is applied to the permeation membrane 4.

The second tensile force T2 that is applied to the permeation membrane 4 in a case where the measurement surface 4b of the permeation membrane 4 is not in a wet state, that is, in a case where the measurement surface 4b is in a dry state in the concentration meter 1 of the present embodiment is higher than the first tensile force T1 that is applied in the case where the measurement surface 4b is in a wet state.

In the permeation membrane 4 to which the second tensile force T2 is applied, the thickness is thinner, and the opening area of the hole 4c is larger, with respect to the permeation membrane 4 to which the first tensile force T1 is applied. Accordingly, in the permeation membrane 4 to which the second tensile force T2 is applied, a permeation amount per unit time period of the measurement target in the liquid 20 increases, with respect to the permeation membrane 4 to which the first tensile force T1 is applied.

Consequently, even when the concentration meter 1 of the present embodiment starts a concentration measuring operation in the state where the measurement surface 4b of the permeation membrane 4 is dry, the concentration meter 1 can allow the measurement target in the liquid 20 that contacts the measurement surface 4b to permeate to the internal liquid 5 side quickly by increasing the tensile force which is applied to the permeation membrane 4, and therefore, can reduce a time period until concentration measurement can be started.

Further, the concentration meter 1 of the present embodiment reduces the tensile force which is applied to the permeation membrane 4 when the measurement surface 4b of the permeation membrane 4 is in a wet state, and concentration measurement is immediately enabled, and therefore can extend life of the permeation membrane 4.

Note that although in the present embodiment which is illustrated, the holding portion 61 directly holds the housing 2, the holding portion 61 may be configured to hold the outer frame 11. In this case, the holding portion 61 indirectly holds the housing 2 via the outer frame 11.

Note that although the actuator 12 of the present embodiment has a configuration that moves the outer frame 11 relative to the housing 2 by changing the air pressure or the liquid pressure in the adjustment chamber 11c by the pump 12a, the configuration of the actuator 12 is not limited to the present embodiment.

Figure 5:
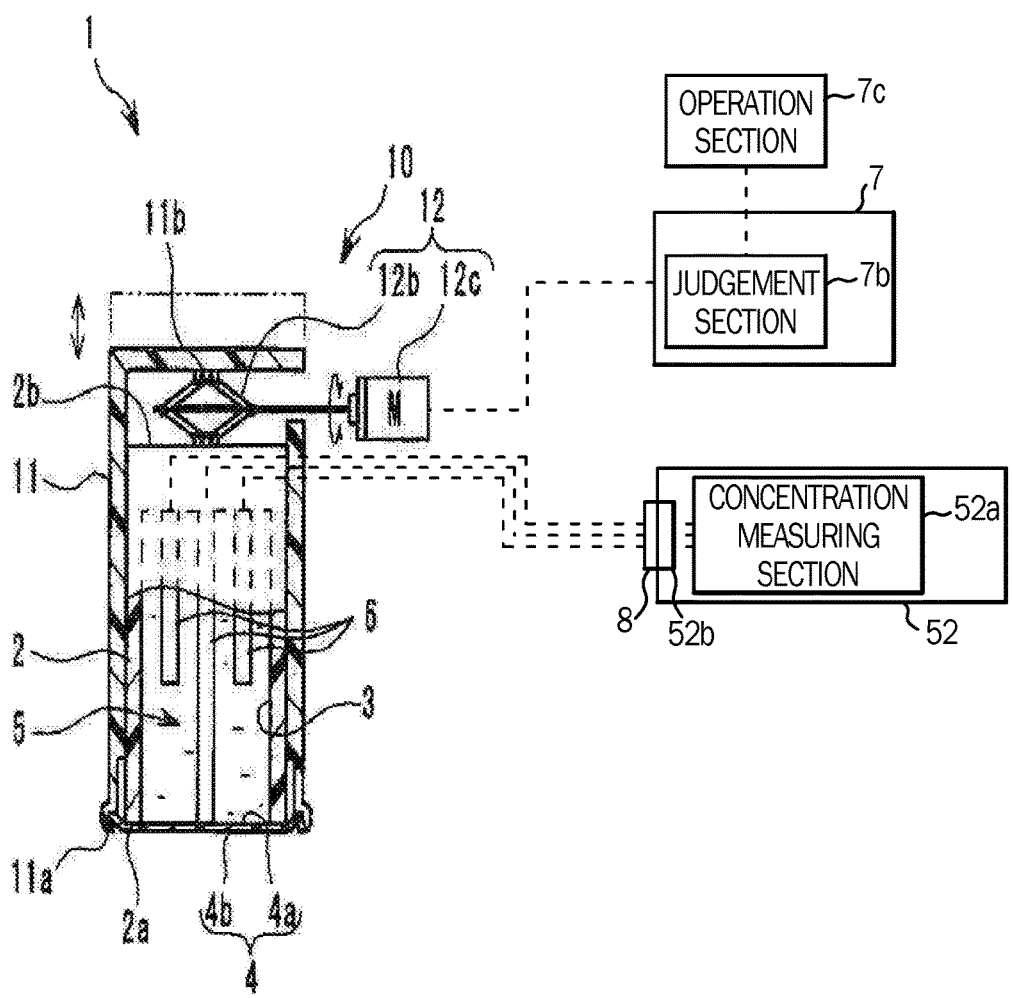
FIG. 5 is a view illustrating a modification of an actuator of the first embodiment.

FIG. 5 illustrates a modification of the actuator 12 of the present embodiment. The actuator 12 of the present modification illustrated in FIG. 5 includes a pantograph jack 12b with which a length in a direction of the advancing and retreating movement of the outer frame 11 relative to the housing 2 changes, and an electric motor 12c that drives the pantograph jack 12b.

The pantograph jack 12b converts a rotational motion of the electric motor 12c into a linear motion along the direction of the advancing and retreating movement of the outer frame 11, and moves the outer frame 11 to advance and retreat with respect to the housing 2 in accordance with extension and contraction. The electric motor 12c is electrically connected to the control section 7, and an operation of the electric motor 12c is controlled by the control section 7.

Second Embodiment

Next, a second embodiment of the present invention will be described. Hereinafter, only difference from the first embodiment will be described, similar components to the components in the first embodiment will be assigned with the same reference signs, and explanation of the similar components will be properly omitted.

Figure 6:
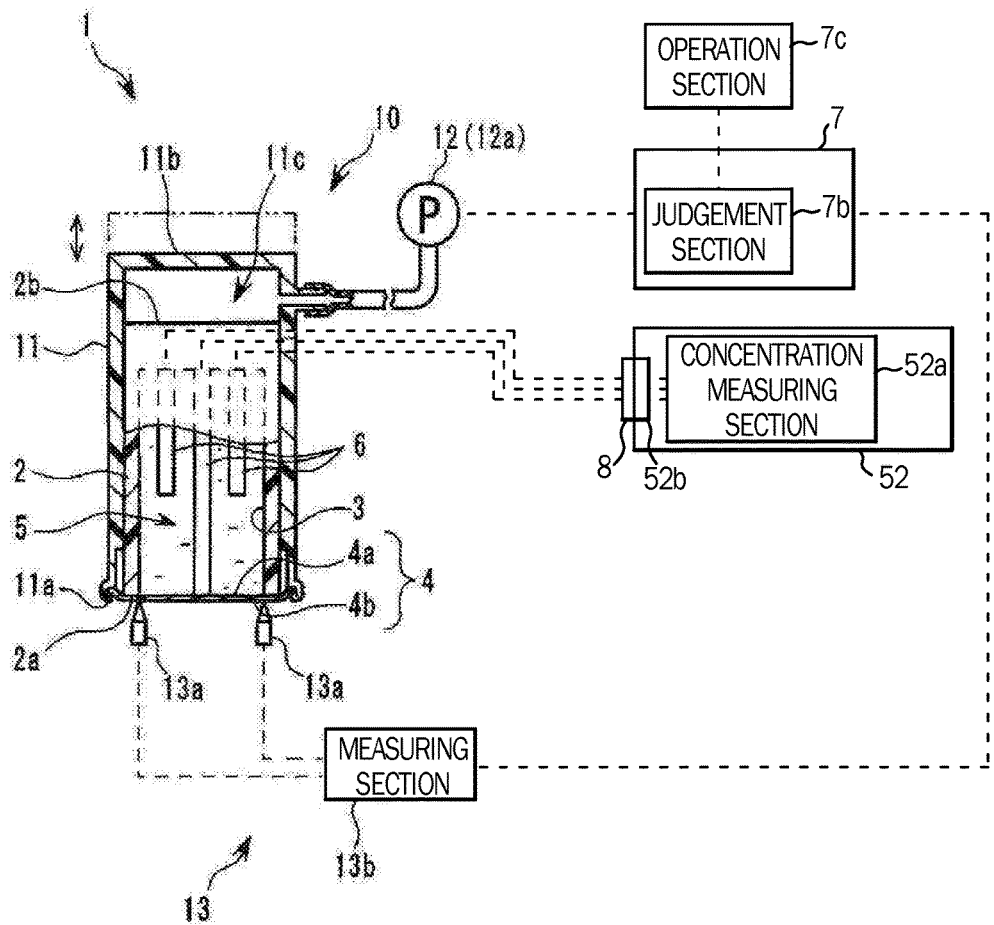
FIG. 6 is a view illustrating a configuration of a concentration meter of a second embodiment.

FIG. 6 is a view illustrating a configuration of the concentration meter 1 of the present embodiment. The concentration meter 1 of the present embodiment differs from the first embodiment in a point that the concentration meter 1 of the present embodiment includes a detection section 13 that detects whether or not the measurement surface 4b of the permeation membrane 4 is in a wet state.

The detection section 13 of the present embodiment includes a pair of electrodes 13a and a measuring section 13b that measures an electric resistance value between the pair of the electrodes 13a. The pair of electrodes 13a are separated from each other by a predetermined distance and contact the measurement surface 4b of the permeation membrane 4. That is, the measuring section 13b measures an electric resistance value of the measurement surface 4b of the permeation membrane 4.

The measuring section 13b is electrically connected to the control section 7, and an operation of the measuring section 13b is controlled by the control section 7. Information on the electric resistance value of the measurement surface 4b of the permeation membrane 4, which is measured by the measuring section 13b, is inputted to the judgment section 7b of the control section 7.

Measurement of the electric resistance value of the measurement surface 4b of the permeation membrane 4 by the measuring section 13b is performed when the measurement surface 4b exists in the air. The judgment section 7b judges that the measurement surface 4b of the permeation membrane 4 is in a wet state when the electric resistance value of the measurement surface 4b of the permeation membrane 4 measured by the measuring section 13b is a predetermined value or less. Further, the judgment section 7b judges that the measurement surface 4b of the permeation membrane 4 is in a dry state when the electric resistance value of the measurement surface 4b of the permeation membrane 4 that is measured by the measuring section 13b exceeds the predetermined value.

Similarly to the first embodiment, the control section 7 controls the adjustment section 10 and sets the tensile force that is applied to the permeation membrane 4 as the first tensile force T1 when the judgment section 7b judges that the measurement surface 4b of the permeation membrane 4 is in a wet state, for example.

Further, when the judgment section 7b judges that the measurement surface 4b of the permeation membrane 4 is not in a wet state, for example, the control section 7 controls the adjustment section 10 and makes the tensile force that is applied the permeation membrane 4 higher than the first tensile force T1.

As described above, the concentration meter 1 of the present embodiment automatically detects whether or not the measurement surface 4b of the permeation membrane 4 is in a wet state, and automatically increases the tensile force which is applied to the permeation membrane 4 when the concentration meter 1 detects that the measurement surface 4b is in a dry state.

In this way, the concentration meter 1 of the present embodiment does not require a judgment operation of the wet state of the measurement surface 4b by the user, and can easily perform concentration measurement.

Further, the concentration meter 1 of the present embodiment can allow the measurement target in the liquid 20 contacting the measurement surface 4b to permeate to the internal liquid 5 side quickly by increasing the tensile force which is applied to the permeation membrane 4, even when the concentration measurement operation is started in the state where the measurement surface 4b of the permeation membrane 4 is dry, as in the first embodiment, and therefore, can reduce the time period until concentration measurement can be started.

Figure 7:
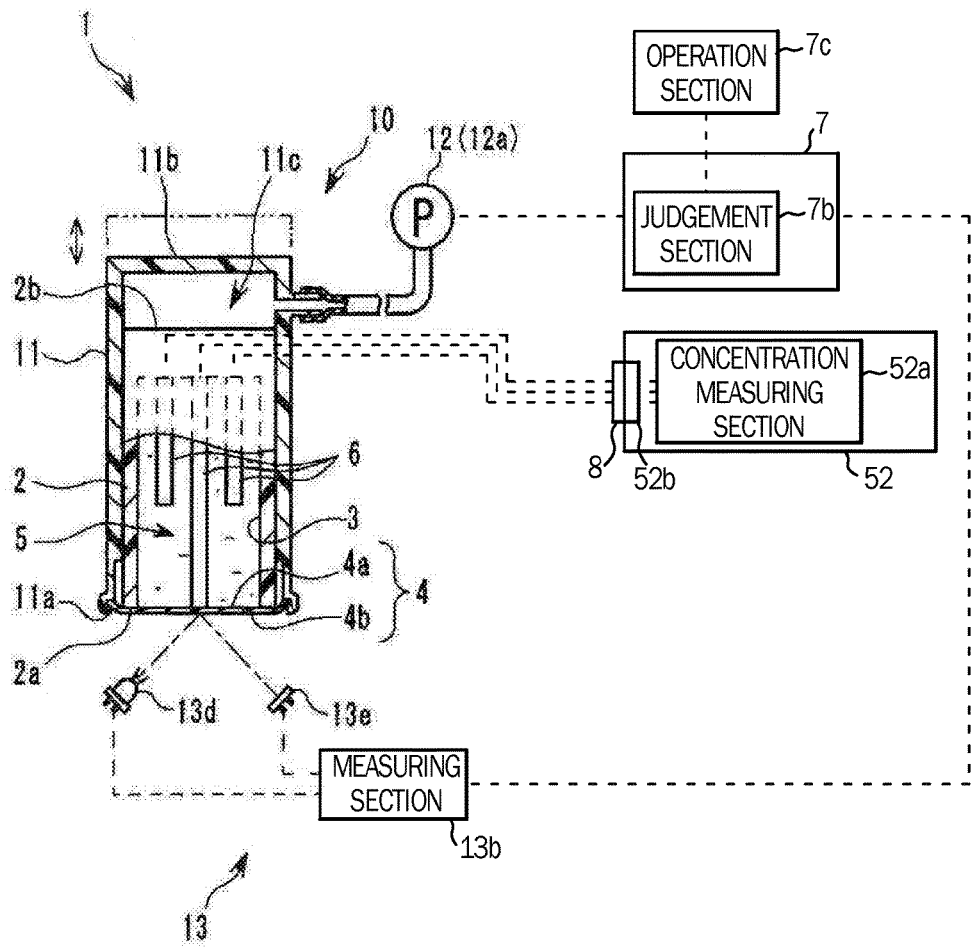
FIG. 7 is a view illustrating a first modification of a detection section of the second embodiment.

Note that the configuration of the detection section 13 is not limited to the present embodiment. FIG. 7 is a view illustrating a first modification of the detection section 13 of the present embodiment. The detection section 13 of the first modification includes a light emitting section 13d such as an LED, and a light receiving section 13e such as a photodiode. The light emitting section 13d and the light receiving section 13e are electrically connected to the measuring section 13b.

The detection section 13 of the first modification emits light to the measurement surface 4b of the permeation membrane 4 from the light emitting section 13d, and measures an intensity of a light that is reflected on the measurement surface 4b, in the light receiving section 13e. That is, the detection section 13 measures a reflectivity of the light on the measurement surface 4b of the permeation membrane 4. Measurement of the reflectivity of the light on the measurement surface 4b of the permeation membrane 4 is performed when the measurement surface 4b exists in the air.

The judgment section 7b of the first modification judges that the measurement surface 4b of the permeation membrane 4 is in a wet state when the reflectivity of the light on the measurement surface 4b of the permeation membrane 4, which is measured by the detection section 13 is a predetermined value or more. Further, the judgment section 7b judges that the measurement surface 4b of the permeation membrane 4 is in a dry state when the reflectivity of the light on the measurement surface 4b of the permeation membrane 4, which is measured by the detection section 13, is below the predetermined value.

Figure 8:
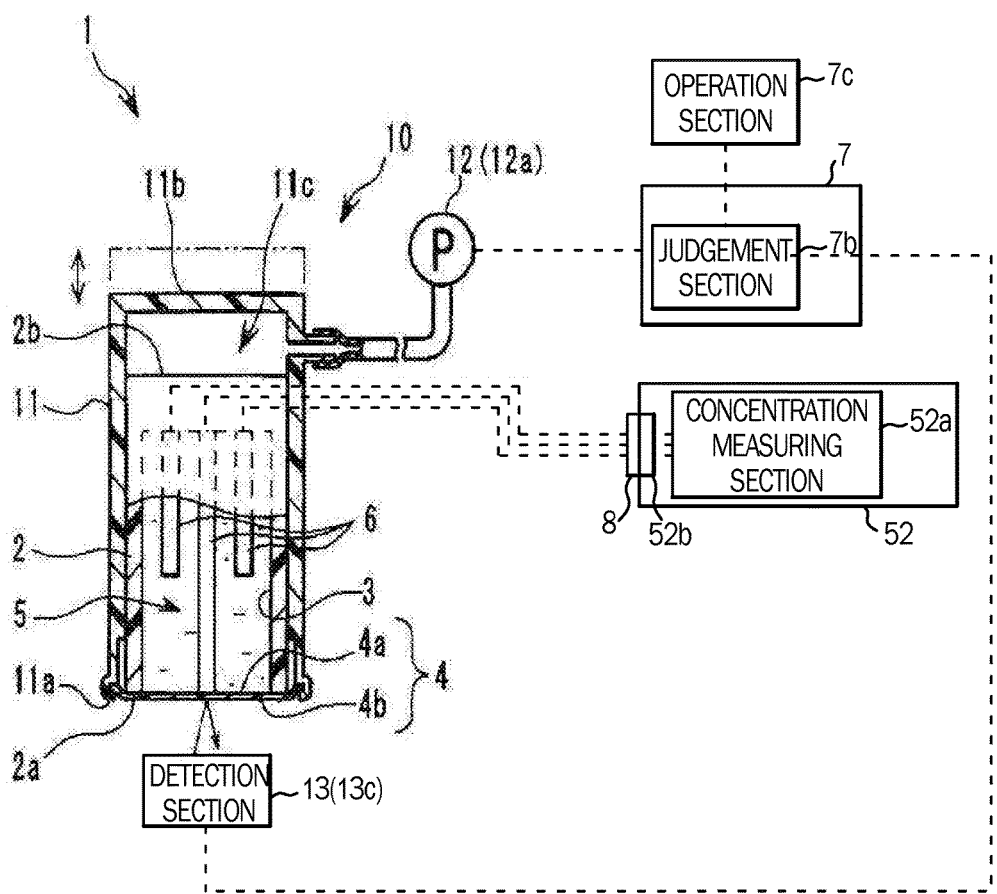
FIG. 8 is a view illustrating a second modification of the detection section of the second embodiment.

FIG. 8 is a view illustrating a second modification of the detection section 13 of the present embodiment. The detection section 13 of the second modification includes a temperature sensor 13c that measures the temperature of the measurement surface 4b of the membrane 4, such as an infrared thermometer.

The temperature sensor 13c is electrically connected to the judgment section 7b, and a measurement result of the temperature of the measurement surface 4b is inputted to the judgment section 7b. Measurement of the temperature of the measurement surface 4b of the permeation membrane 4 by the detection section 13 is performed when the measurement surface 4b exists in the air.

The judgment section 7b of the first modification judges that the measurement surface 4b of the permeation membrane 4 is in a wet state when the temperature of the measurement surface 4b of the permeation membrane 4 which is measured by the detection section 13 is lower than an ambient temperature. This is because when the measurement surface 4b is in a wet state, the temperature of the measurement surface 4b becomes lower than the ambient temperature as a result that a liquid evaporates from the measurement surface 4b. Further, the judgment section 7b judges that the measurement surface 4b of the permeation membrane 4 is in a dry state, when the temperature of the measurement surface 4b of the permeation membrane 4, which is measured by the detection section 13, is the ambient temperature or higher.

Third Embodiment

Next, a third embodiment of the present invention will be described. Hereinafter, only difference from the first and the second embodiments will be described, similar components to the components in the first and the second embodiments will be assigned with the same reference signs, and explanation of the similar components will be properly omitted.

Figure 9:
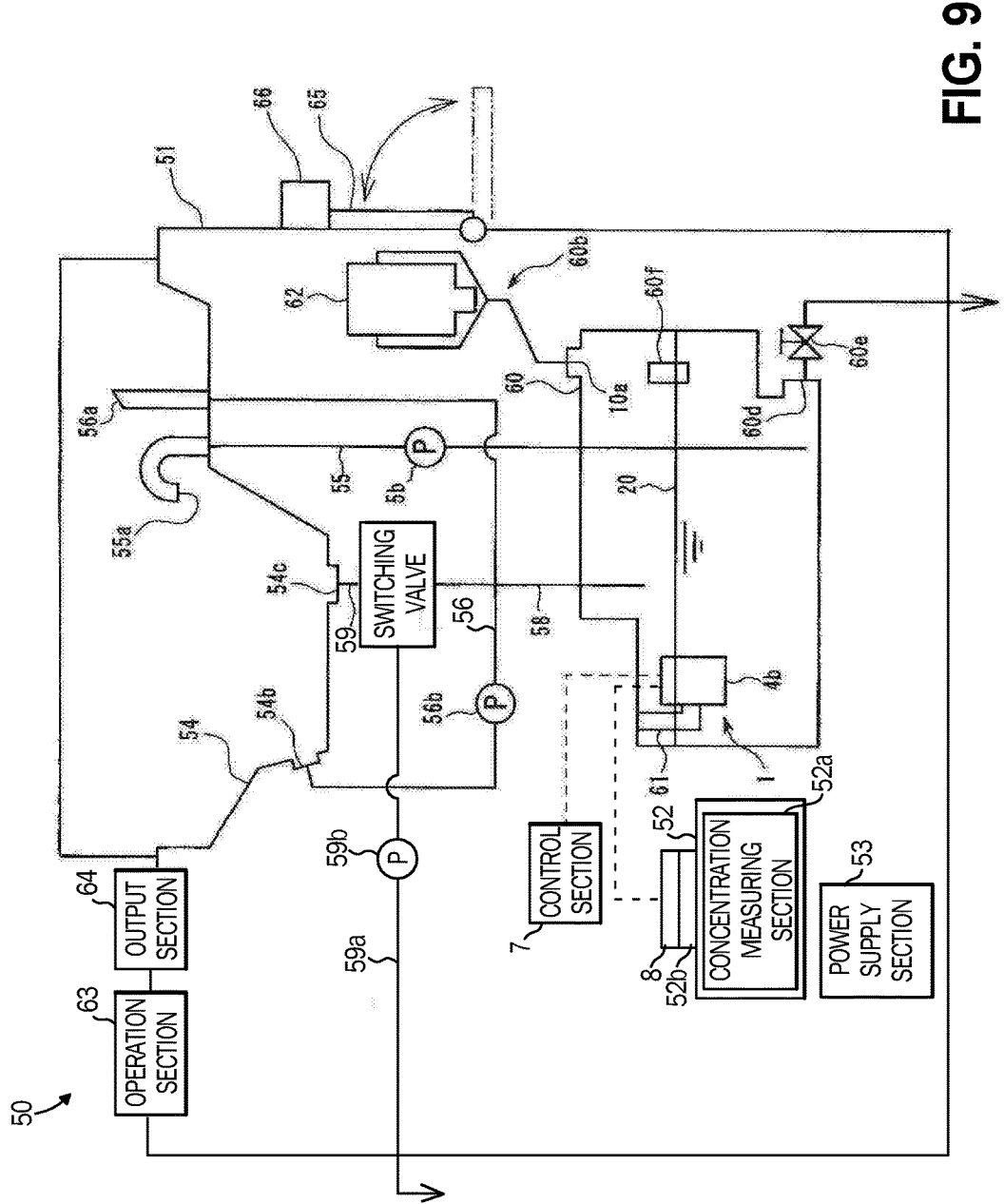
FIG. 9 is a diagram illustrating a configuration of an endoscope reprocessor of a third embodiment.

An endoscope reprocessor 50 illustrated in FIG. 9 is an apparatus that applies reprocessing to an endoscope. Although the reprocessing mentioned here is not specially limited, cleaning treatment that removes contamination by organic substances and the like with use of the liquid 20, disinfecting treatment that makes predetermined microorganisms ineffective, or sterilizing treatment that excludes or eliminates all microorganisms is cited, for example.

As illustrated in FIG. 9, the endoscope reprocessor 50 includes the concentration meter 1, the control section 52, a power supply section 53, a treatment tank 54, the medicinal solution tank 60 and the holding portion 61. The concentration meter 1, the control section 52, the power supply section 53, the treatment tank 54, the medicinal solution tank 60 and the holding portion 61 are placed in the endoscope reprocessor main body 51.

The control section 52 is configured by including an arithmetic device (CPU), a storage device (RAM), an auxiliary storage device, an input/output device, a power control device and the like, and has a configuration that controls actions of respective parts that configure the endoscope reprocessor 50 based on a predetermined program. Actions of the respective components that are included in the endoscope reprocessor 50 in the following explanation are controlled by the control section 52 even when explanation is not specially made. Note that the control section 52 may also serve as the control section 7 of the concentration meter 1. The control section 52 may include the aforementioned concentration measuring section 52a.

The power supply section 53 supplies electric power to the respective parts of the endoscope reprocessor 50. In the present embodiment, as one example, the power supply section 53 distributes electric power that is obtained from an outside such as a commercial power supply to the respective parts. Note that the power supply section 53 may include a power generating device and a battery.

The treatment tank 54 is in a concave shape having an opening portion that opens upward, and can store a liquid inside. In the treatment tank 54, an endoscope not illustrated can be disposed. An opening at an upper part of the treatment tank 54 may be configured to be closable by a lid. In the treatment tank 54, a medicinal solution nozzle 55a and a liquid discharge port 54c are provided.

The medicinal solution nozzle 55a is an opening portion that communicates with the medicinal solution tank 60 via a medicinal solution conduit 55. The medicinal solution tank 60 stores the liquid 20 that is a medicinal solution for use in reprocessing. Although a kind of the liquid 20 that is stored by the medicinal solution tank 60 is not specially limited, in the present embodiment, as one example, the liquid 20 is a disinfectant liquid such as a peracetic acid that is used in disinfecting treatment. Note that the liquid 20 may be a cleaning solution or the like for use in cleaning treatment. In the medicinal solution conduit 55, a medicinal solution pump 55b is provided. By the medicinal solution pump 55b being operated, the liquid 20 in the medicinal solution tank 60 is transferred into the treatment tank 54.

The liquid discharge port 54c is an opening portion that is provided at a lowest spot in the treatment tank 54. The liquid discharge port 54c is connected to a discharge conduit 59. The discharge conduit 59 causes the liquid discharge port 54c and a switching valve 57 to communicate with each other. A collection conduit 58 and a disposal conduit 59a are connected to the switching valve 57. The switching valve 57 can switch the discharge conduit 59 to a state where the discharge conduit 59 is closed, a state where the discharge conduit 59 and the collection conduit 58 communicate with each other, or a state where the discharge conduit 59 and the discarding conduit 59a communicate with each other.

The collection conduit 58 causes the medicinal solution tank 60 and the switching valve 57 to communicate with each other. Further, a discharge pump 59b is provided in the discarding conduit 59a. The discarding conduit 59a is connected to a liquid discharge facility for receiving the liquid that is discharged from the endoscope reprocessor 50.

When the switching valve 57 is brought into a closed state, a liquid can be stored in the treatment tank 54. Further, when the switching valve 57 is brought into the state where the discharge conduit 59 and the collection conduit 58 communicate with each other when the liquid 20 is stored in the treatment tank 54, the liquid 20 is transferred to the medicinal solution tank 60 from the treatment tank 54. Further, when the switching valve 57 is brought into the state where the discharge conduit 59 and the discarding conduit 59a communicate with each other, and an operation of the discharge pump 59b is started, the liquid in the treatment tank 54 is pumped out to the liquid discharge facility via the discarding conduit 59a.

Further, a circulation port 54b and a circulation nozzle 56a are provided in the treatment tank 54. The circulation port 54b and the circulation nozzle 56a communicate with each other via a circulation conduit 56. In the circulation conduit 56, a circulation pump 56b is provided.

An operation of the circulation pump 56b is performed, whereby the liquid in the treatment tank 54 is sucked out from the circulation port 54b, and thereafter, returns into the treatment tank 54 via the circulation conduit 56 and the circulation nozzle 56a. The endoscope reprocessor 50 houses the endoscope in the treatment tank 54, causes the liquid 20 stored in the treatment tank 54 to circulate, and thereby executes disinfecting treatment or the like to the endoscope.

In the medicinal solution tank 60, a medicinal solution introduction port 60a and a medicinal solution discharge port 60d are provided. The medicinal solution introduction port 60a is an opening portion that is provided in the medicinal solution tank 60. The medicinal solution introduction port 60a communicates with a medicinal solution supply section 60b.

The medicinal solution supply section 60b supplies the liquid 20 to the medicinal solution tank 60. In the present embodiment, as one example, the medicinal solution supply section 60b has a configuration that causes a medicinal solution bottle 62 in which the unused liquid 20 is stored and the medicinal solution introduction port 60a to communicate with each other. The medicinal solution bottle 62 is connected to the medicinal solution supply section 60b, whereby the unused liquid 20 is introduced into the medicinal solution tank 60 via the medicinal solution supply section 60b and the medicinal solution introduction port 60a from the medicinal solution bottle 62.

The medicinal solution discharge port 60d is an opening portion that is provided in a bottom portion of the medicinal solution tank 60. In the medicinal solution discharge port 60d, a discharge valve 60e that opens and closes the medicinal solution discharge port 60d is provided.

When the discharge valve 60e is brought into a closed state, the liquid 20 can be stored in the medicinal solution tank 60. Further, when the discharge valve 60e is brought into an opened state, the liquid 20 in the medicinal solution tank 60 is discharged from the endoscope reprocessor 50, and an inside of the medicinal solution tank 60 can be brought into an empty state.

A water level gauge 60f detects whether or not a liquid surface of the liquid 20 that is stored in the medicinal solution tank 60 reaches a predetermined height in the medicinal solution tank 60. The water level gauge 60f is electrically connected to the control section 52, and outputs information on a detection result to the control section 52. Note that the medicinal solution tank 60 may have a configuration that introduces tap water and mixes the tap water and the liquid 20 at a predetermined ratio.

Further, lower than a predetermined height in the medicinal solution tank 60, the measurement surface 4b of the concentration meter 1 is exposed. In other words, the measurement surface 4b of the concentration meter 1 is held by the holding portion 61 so as to be immersed in the liquid 20 that is stored in the medicinal solution tank 60. Note that in the state where the concentration meter 1 is held by the holding portion 61, the main body connection section 8 of the concentration meter 1 and the electric contact point 52b which is electrically connected to the concentration measuring section 52a contact each other.

The endoscope reprocessor 50 includes a bottle replacement door 65 that is opened and closed when the medicinal solution bottle 62 is replaced, and a door lock 66 that locks the bottle replacement door 65. Note that the bottle replacement door 65 is not limited to a rotary type, but may be of a slide type and a drawing type. A user can replace the medicinal solution bottle 62 which is connected to the medicinal solution supply section 60b when the bottle replacement door 65 is in an opened state. The door lock 66 is electrically connected to the control section 52, and an operation of the door lock 66 is controlled by the control section 52.

Further, the endoscope reprocessor 1 includes an operation section 63 and an output section 64, which configure a user interface that performs exchange of information with the user. The operation section 63 and the output section 64 are electrically connected to the control section 52. Note that the operation section 63 and the output section 64 may be in a mode included in an electronic apparatus that performs wireless communication with the control section 52.

The operation section 63 includes an operation member such as a push switch and a touch sensor. Further, the output section 64 includes a display device that displays images and characters, a light emitting device that emits light, a speaker that generates sound or a combination of the display device, the light emitting device and the speaker, for example.

Figure 10:
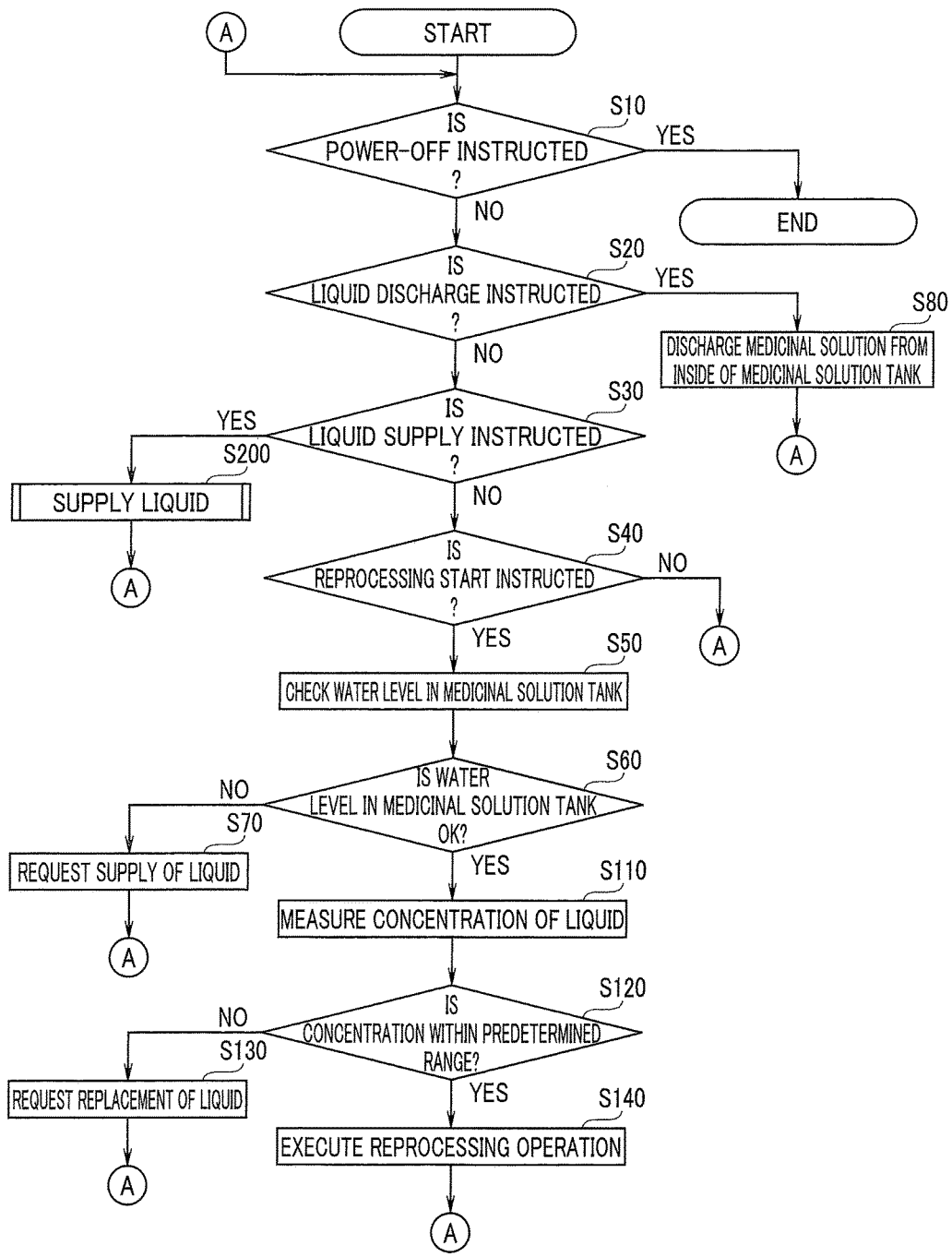
FIG. 10 is a flowchart illustrating an operation of the endoscope reprocessor of the third embodiment.

Next, an operation of the endoscope reprocessor 50 having the aforementioned configuration will be described with reference to flowcharts illustrated in FIG. 10 and FIG. 11. The flow illustrated in FIG. 10 is started when the power supply of the endoscope reprocessor 50 is brought into an on state, for example. Note that input of an operation instruction to the endoscope reprocessor 50 from the user is performed through the operation section 63.

After the power supply of the endoscope reprocessor 50 is brought into an on state, initialization actions of the respective components are executed first, and as shown in steps S10 and S40, a standby state in which the endoscope reprocessor 50 is on standby until input of an instruction from the user is performed is executed.

More specifically, in step S10, it is judged whether or not an instruction to turn off the power supply is inputted by the user. When it is judged that the instruction to turn off the power supply is inputted in step S10, the flow shifts to a state where the power supply is turned off, and the flow illustrated in FIG. 10 is ended. When it is judged that the instruction to turn off the power supply is not inputted in step S10, the flow shifts to step S20.

In step S20, it is judged whether or not an instruction to discharge the liquid 20 in the medicinal solution tank 60 from the endoscope reprocessor 50 is inputted by the user. An operation of discharging the liquid 20 from the endoscope reprocessor 50 is executed when the liquid 20 in the medicinal solution tank 60 is replaced, and when the endoscope reprocessor 50 is not used for a relatively long period, for example.

When it is judged that the instruction to discharge the liquid 20 in the medicinal solution tank 60 is inputted in step S20, the flow shifts to step S80 and a discharge step is executed. In step S80, the discharge valve 60e is brought into an opened state, and the liquid 20 in the medicinal solution tank 60 is discharged to an outside of the endoscope reprocessor 50 via the medicinal solution discharge port 60d. After the liquid 20 in the medicinal solution tank 60 is discharged, the discharge valve 60e is brought into a closed state. After execution of step S80, the inside of the medicinal solution tank 60 is in an empty state until the unused liquid 20 is newly supplied via the medicinal solution supply section 60b.

When it is judged that the instruction to discharge the liquid 20 in the medicinal solution tank 60 is not inputted in step S20, the flow shifts to step S30.

In step S30, it is judged whether or not an instruction to supply the unused liquid 20 into the medicinal solution tank 60 is inputted by the user. When it is judged that the instruction to supply the liquid 20 into the medicinal solution tank 60 is inputted in step S30, a liquid supply step in step S200 that will be described later is executed. When it is judged that the instruction to supply the liquid 20 into the medicinal solution tank 60 is not inputted in step S30, the flow shifts to step S40.

In step S40, it is judged whether or not an instruction to execute reprocessing to the endoscope is inputted by the user. When it is judged that the instruction to execute the reprocessing is inputted in step S40, the flow shifts to step S50 that will be described later. When it is judged that the instruction to execute the reprocessing is not inputted in step S40, the flow returns to step S10.

In step S50, it is confirmed whether or not the liquid 20 is stored up to a predetermined level in the medicinal solution tank 60 by the water level gauge 60f. When it is judged that the liquid 20 is not stored up to the predetermined level in the medicinal solution tank 60 in step S50 (NO in step S60), the flow shifts to step S70.

In step S70, an output requesting supply of the liquid 20 into the medicinal solution tank 60 of the user is executed via the output section 64. After execution of step S70, the flow returns to step S10. That is, in the endoscope reprocessor 50 of the present embodiment, reprocessing to the endoscope is not started until the liquid 20 is supplied into the medicinal solution tank 60 up to the predetermined level by the user.

Further, when it is judged that the liquid 20 is stored up to the predetermined level in the medicinal solution tank 60 in step S50 (YES in step S60), the flow shifts to step S110.

In step S110, concentration measurement of the liquid 20 is executed by the concentration meter 1. Next, in step S120, it is judged whether or not the measurement value of the concentration of the liquid 20 is within a predetermined range. The predetermined range of the concentration refers to a range in which the liquid 20 exhibits a medicinal effect that is needed to execute the reprocessing.

When it is judged that the measurement value of the concentration of the liquid 20 is within the predetermined range in step S120, the flow shifts to step S140, and reprocessing to the endoscope is executed. The reprocessing to the endoscope includes disinfecting treatment that guides the liquid 20 into the treatment tank 54 and immerses the endoscope in the liquid 20.

In the disinfecting treatment, the medicinal solution pump 55b is operated after the switching valve 57 is brought into a closed state, and the liquid 20 is transferred into the treatment tank 54 in which the endoscope is disposed, from the inside of the medicinal solution tank 60. Subsequently, after the liquid 20 is stored up to the predetermined level in the treatment tank 54, the medicinal solution pump 55b is stopped, and an operation of the circulation pump 56b is performed for a predetermined time period. Subsequently, after stop of the circulation pump 56b, the switching valve 57 is brought into a state where the discharge conduit 59 and the collection conduit 58 communicate with each other, the liquid 20 in the treatment tank 54 is collected into the medicinal solution tank 60.

After end of the reprocessing in step S140, the flow returns to step S10.

When it is judged that the measurement value of the concentration of the liquid 20 is outside the predetermined range in step S120, the flow shifts to step S130. In step S130, an output that requests the user to execute a replacement operation of the liquid 20 so as to discharge the liquid 20 in the medicinal solution tank 60 and newly supply the unused liquid 20 into the medicinal solution tank 60, via the output section 64. After execution of step S130, the flow returns to step S10.

That is, in the endoscope reprocessor 50 of the present embodiment, reprocessing to the endoscope is not started until the liquid 20 with the concentration being within the predetermined range is stored in the medicinal solution tank 60.

Figure 11:
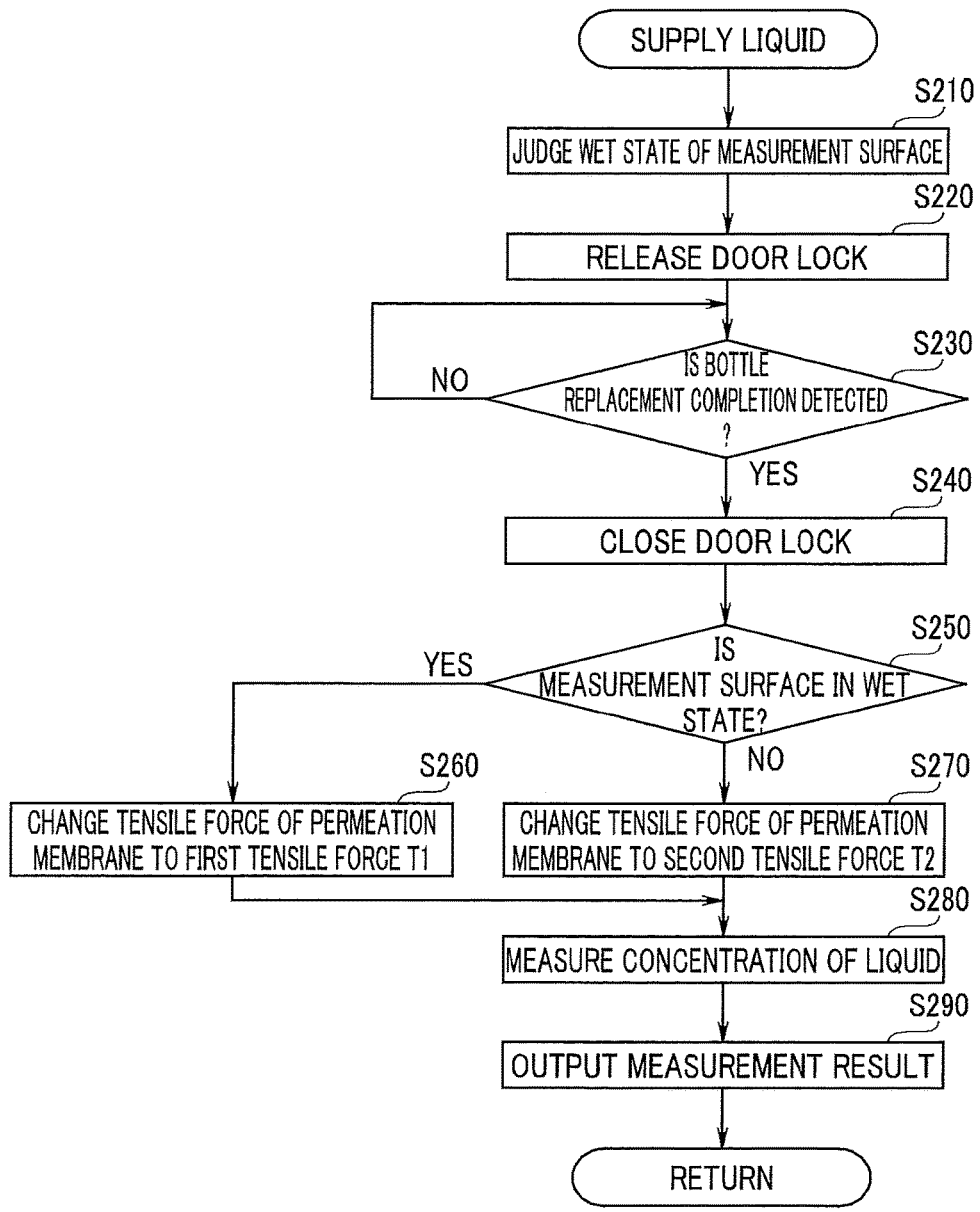
FIG. 11 is a flowchart illustrating a liquid supply process of the third embodiment.

FIG. 11 is a flowchart of a liquid supply process that supplies the liquid 20 into the medicinal solution tank 60, in step S200. As described above, the liquid supply process is executed when an instruction to supply the liquid 20 into the medicinal solution tank 60 is inputted by the user.

In the liquid supply process, it is judged whether or not the measurement surface 4b of the permeation membrane 4 is in a wet state by the judgment section 7b of the concentration meter 1 first in step S210. The judgment by the judgment section 7b may be the mode based on the operation by the user as in the first embodiment, or may be the mode in which the judgment is automatically performed by using the detection section 13 as in the second embodiment.

Next, in step S220, the door lock 66 is brought into a released state. By execution of step S220, opening and closing of the bottle replacement door 65 are enabled.

Next, in step S230, the flow is on standby until the replacement operation of the medicinal solution bottle 62 that is performed by the user is completed. For example, when it is detected that the bottle replacement door 65 is closed by the user, it is judged that the replacement operation of the medicinal solution bottle 62 is completed.

At a time point of completion of step S230, the unused liquid 20 in the medicinal solution bottle 62 is supplied into the medicinal solution tank 60 via the medicinal solution supply section 60b. Note that after completion of step S230, a step of mixing tap water and the liquid 20 at a predetermined ratio in the medicinal solution tank 60 may be executed.

In next step S250, the flow is branched based on the judgment result in step S210. When it is judged that the measurement surface 4b of the permeation membrane 4 is in a wet state in step S210, the flow shifts to step S260. In step S260, the adjustment section 10 of the concentration meter 1 is controlled to set the tensile force that is applied to the permeation membrane 4 at the first tensile force T1.

When it is judged that the measurement surface 4b of the permeation membrane 4 is not in a wet state, but in a dry state in step S210, the flow shifts to step S270. In step S270, the adjustment section 10 of the concentration meter 1 is controlled to set the tensile force that is applied to the permeation membrane 4 at the second tensile force T2.

Subsequently, in step S280, the concentration of the liquid 20 that is stored in the medicinal solution tank 60 is measured, and in step S290, the result of the concentration measurement of the liquid 20 is outputted from the output section 64. The user can judge whether or not the liquid 20 which is newly supplied into the medicinal solution tank 60 is usable based on the measurement result which is outputted by the output section 64.

When the liquid supply process that supplies the liquid 20 into the medicinal solution tank 60 is performed after the state where the inside of the medicinal solution tank 60 is empty is kept for a relatively long time period, the measurement surface 4b of the permeation membrane 4 of the concentration meter 1 is likely to be in a dry state. Thus, in the endoscope reprocessor 50 of the present embodiment, it is judged whether or not the measurement surface 4b of the permeation membrane 4 is in a wet state at the time of the liquid supply process being carried out, and when it is detected that the measurement surface 4b is in a dry state, the tensile force which is applied to the permeation membrane 4 is increased. Consequently, even when the concentration measurement operation is started in the state where the measurement surface 4b of the permeation membrane 4 is dry, the tensile force which is applied to the permeation membrane 4 is increased, and the measurement target in the liquid 20 which contacts the measurement surface 4b can be allowed to permeate to the internal liquid 5 side quickly, so that the time period until the concentration measurement can be started can be reduced.

For example, in the endoscope reprocessor 50 of the present embodiment, concentration measurement of the liquid 20 by the concentration meter 1 can be executed without a standby time period being provided after the liquid 20 in the medicinal solution tank 60 is replaced, so that the time period that is required to perform reprocessing to the endoscope can be reduced.

Fourth Embodiment

Next, a fourth embodiment of the present invention will be described. Hereinafter, only difference from the first to the third embodiments will be described, similar components to the components in the first to the third embodiments will be assigned with the same reference signs, and explanation of the similar components will be properly omitted.

Figure 12:
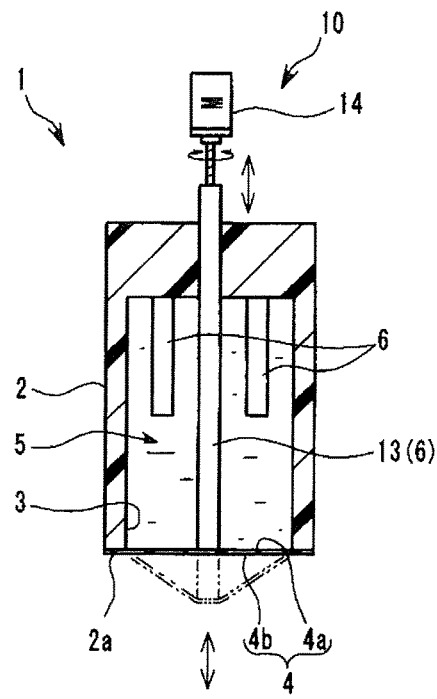
FIG. 12 is a view illustrating a configuration of a concentration meter of a fourth embodiment.

The concentration meter 1 of the present embodiment illustrated in FIG. 12 differs from the first to the third embodiments in the configuration of the adjustment section 10 that applies a mechanical load to the permeation membrane 4.

As illustrated in FIG. 12, the permeation membrane 4 of the present embodiment is provided by being stretched at the distal end portion 2a of the housing 2 in such a manner as to seal the cavity 3.

The adjustment section 10 includes a rod 13 that is placed in the cavity 3 and moves to advance and retreat in a direction orthogonal to the releasing surface 4a of the permeation membrane 4, and an actuator 14 that drives the rod 13. The rod 13 extends in the direction orthogonal to the releasing surface 4a of the permeation membrane 4, in the cavity 3. A distal end portion 13a of the rod 13 abuts on the releasing surface 4a of the permeation membrane 4. A proximal end portion 13b of the rod 13 protrudes to an outside of the housing 2, and is connected to the actuator 14. In the present embodiment, as an example, a part of the rod 13 configures the electrode 6.

The actuator 10b includes an electric motor, and a mechanism that converts a rotational motion of the electric motor into a linear motion, and drives the rod 13 in the direction orthogonal to the releasing surface 4a in accordance with rotation of the electric motor.

The adjustment section 10 of the present embodiment changes a tensile force that is applied to the permeation membrane 4 by pressing the permeation membrane 4 that is held by the housing 2 by the distal end portion 13a of the rod 13 from an inside of the cavity 3. In other words, the adjustment section 10 applies a stress that deforms the permeation membrane 4 so that the measurement surface 4b of the permeation membrane 4 is in a convex shape. The stress that is applied to the permeation membrane 4 by the adjustment section 10 is substantially perpendicular to the surface of the permeation membrane 4.

It is similar to the first to the third embodiments that the thickness of the permeation membrane 4 and the opening area of the hole 4c change by the adjustment section 10 changing the tensile force that is applied to the permeation membrane 4.

Accordingly, even when the concentration measuring operation is started in the state where the measurement surface 4b of the permeation membrane 4 is dry, the concentration meter 1 and the endoscope reprocessor including the concentration meter 1 of the present embodiment can cause the measurement target in the liquid 20 that contacts the measurement surface 4b to permeate to the internal liquid 5 side quickly by increasing the tensile force which is applied to the permeation membrane 4, and therefore the time period until concentration measurement can be started can be reduced.

Fifth Embodiment

Next, a fifth embodiment of the present invention will be described. Hereinafter, only difference from the first to the third embodiments will be described, similar components to the components in the first to the third embodiments will be assigned with the same reference signs, and explanation of the similar components will be properly omitted.

Figure 13:
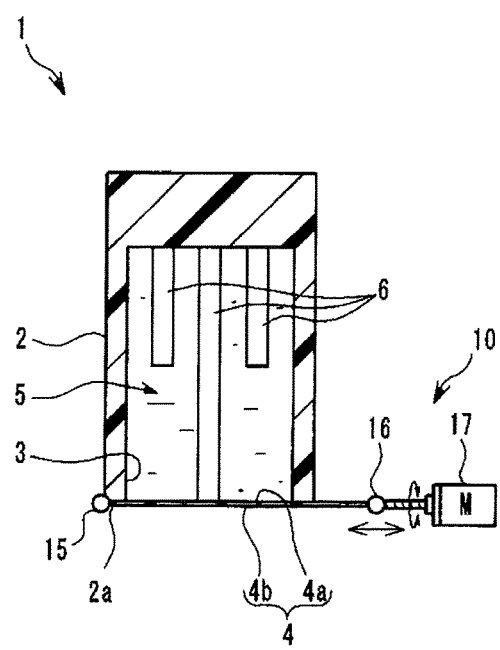
FIG. 13 is a view illustrating a configuration of a concentration meter of a fifth embodiment.
Figure 14:
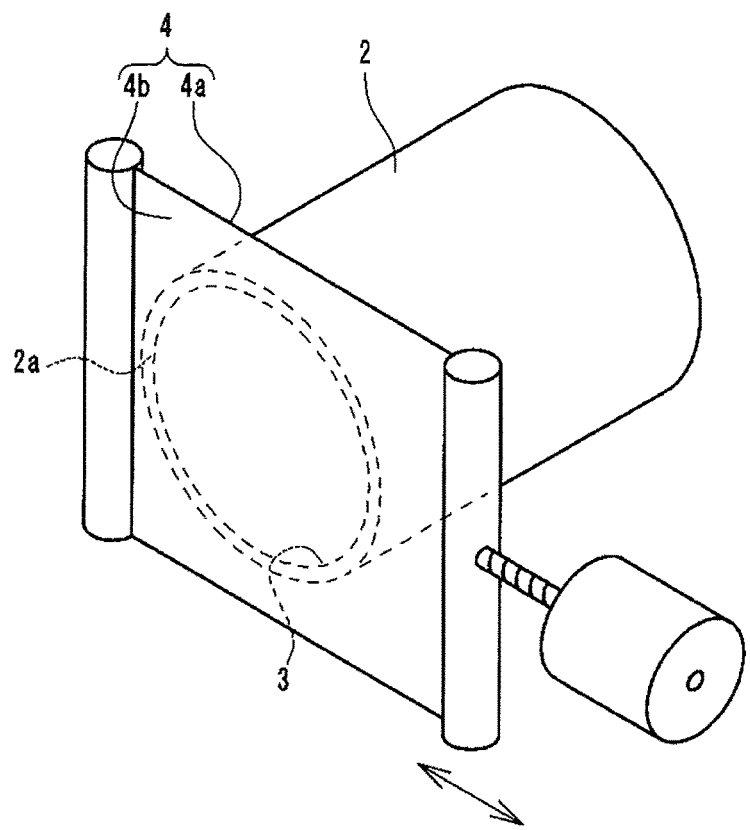
FIG. 14 is a perspective view showing the configuration of the concentration meter of the fifth embodiment.

The concentration meter 1 of the present embodiment illustrated in FIG. 13 and FIG. 14 differs from the first to the third embodiments in the configuration of the adjustment section 10 that applies a mechanical load to the permeation membrane 4. The adjustment section 10 of the present embodiment includes a first holding portion 15, a second holding portion 16 and an actuator 17.

The permeation membrane 4 of the present embodiment is in a rectangular shape. To respective two parallel sides of an outer shape of the permeation membrane 4, the first holding portion 15 and the second holding portion 16 which are the rectilinear rod-shaped members are fixed. That is, the first holding portion 15 and the second holding portion 16 extend parallel with each other, and the permeation membrane 4 is provided by being stretched between the first holding portion 15 and the second holding portion 16.

A position of the first holding portion 15 is fixed with respect to the housing 2. Further, the second holding portion 16 is movable to advance and retreat with respect to the housing 2. The second holding portion 16 moves to advance and retreat in a direction orthogonal to an extending direction of the first holding portion 15 and the second holding portion 16, in a plane parallel with the surface of the permeation membrane 4. The actuator 17 includes, for example, an electric motor, and a mechanism that converts a rotational motion of the electric motor into a linear motion, and drives the second holding portion 16 in accordance with rotation of the electric motor.

The adjustment section 10 of the present embodiment changes a separation distance between the first holding portion 15 and the second holding portion 16, and changes a tensile force that is applied to the permeation membrane 4 that is provided by being stretched between the first holding portion 15 and the second holding portion 16, by driving the second holding portion 16 by the actuator 17.

It is similar to the first to the third embodiments that the thickness of the permeation membrane 4 and the opening area of the hole 4c are changed by the adjustment section 10 changing the tensile force that is applied to the permeation membrane 4.

Accordingly, even when a concentration measurement operation is started in the state where the measurement surface 4b of the permeation membrane 4 is dry, the concentration meter 1 and the endoscope reprocessor including the concentration meter 1 of the present embodiment can cause the measurement target in the liquid 20 that contacts the measurement surface 4b to permeate to the internal liquid 5 side quickly by increasing the tensile force which is applied to the permeation membrane 4, and therefore, can reduce the time period until concentration measurement can be started.

Figure 15:
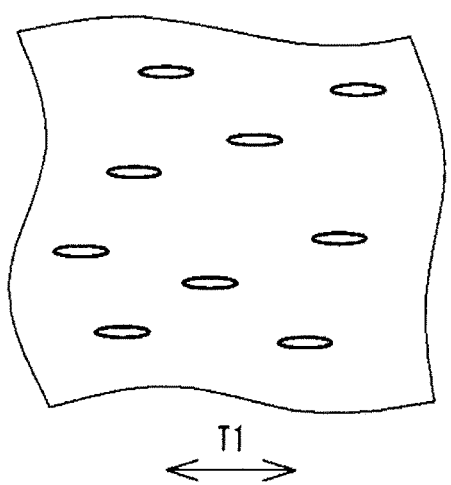
FIG. 15 is a partially enlarged view illustrating a modification of a permeation membrane of the fifth embodiment.
Figure 16:
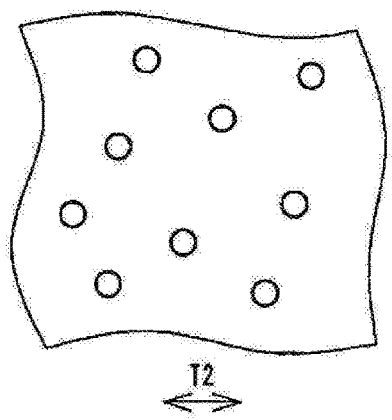
FIG. 16 is a partially enlarged view illustrating a modification of the permeation membrane of the fifth embodiment.

FIG. 15 and FIG. 16 illustrate modifications of the permeation membrane 4 of the present embodiment. FIG. 15 and FIG. 16 are each partial enlarged view of the measurement surface 4b of the permeation membrane 4 of the present modifications. FIG. 15 illustrates opening shapes of a plurality of holes 4c of the permeation membrane 4 in a case where the first tensile force T1 is applied. FIG. 16 illustrates opening shapes of the plurality of holes 4c of the permeation membrane 4 in a case where the second tensile force T2 is applied. In FIG. 15 and FIG. 16, directions of the tensile forces which are applied to the permeation membrane 4 are left and right directions when one faces the drawings as illustrated by arrows in the drawings.

In the present modifications, the first tensile force T1 which is applied to the permeation membrane 4 when the measurement surface 4b of the permeation membrane 4 is in a wet state is lower than the second tensile force T2 which is applied to the permeation membrane 4 when the measurement surface 4b is in a dry state.

The opening shapes of the plurality of holes 4c of the permeation membrane 4 are substantially circular shapes when the second tensile force T2 is applied to the permeation membrane 4, as illustrated in FIG. 16. The opening shapes of the plurality of holes 4c in the case where the first tensile force T1 which is higher than the second tensile force T2 is applied to the permeation membrane 4 are substantially elliptical shapes in which long axes are substantially parallel with the direction in which the tensile force is applied, as illustrated in FIG. 15.

In the present modifications, in the permeation membrane 4 to which the second tensile force T2 is applied, the width of the opening of the hole 4c is larger than in the permeation membrane 4 to which the first tensile force T1 is applied. Accordingly, in the permeation membrane 4 to which the second tensile force T2 is applied, a permeation amount per unit time period of the measurement target in the liquid 20 increases with respect to the permeation membrane 4 to which the first tensile force T1 is applied.

Sixth Embodiment

Next, a sixth embodiment of the present invention will be described. Hereinafter, only difference from the first to the third embodiments will be described, similar components to the components in the first to the third embodiments will be assigned with the same reference signs, and explanation of the similar components will be properly omitted.

Figure 17:
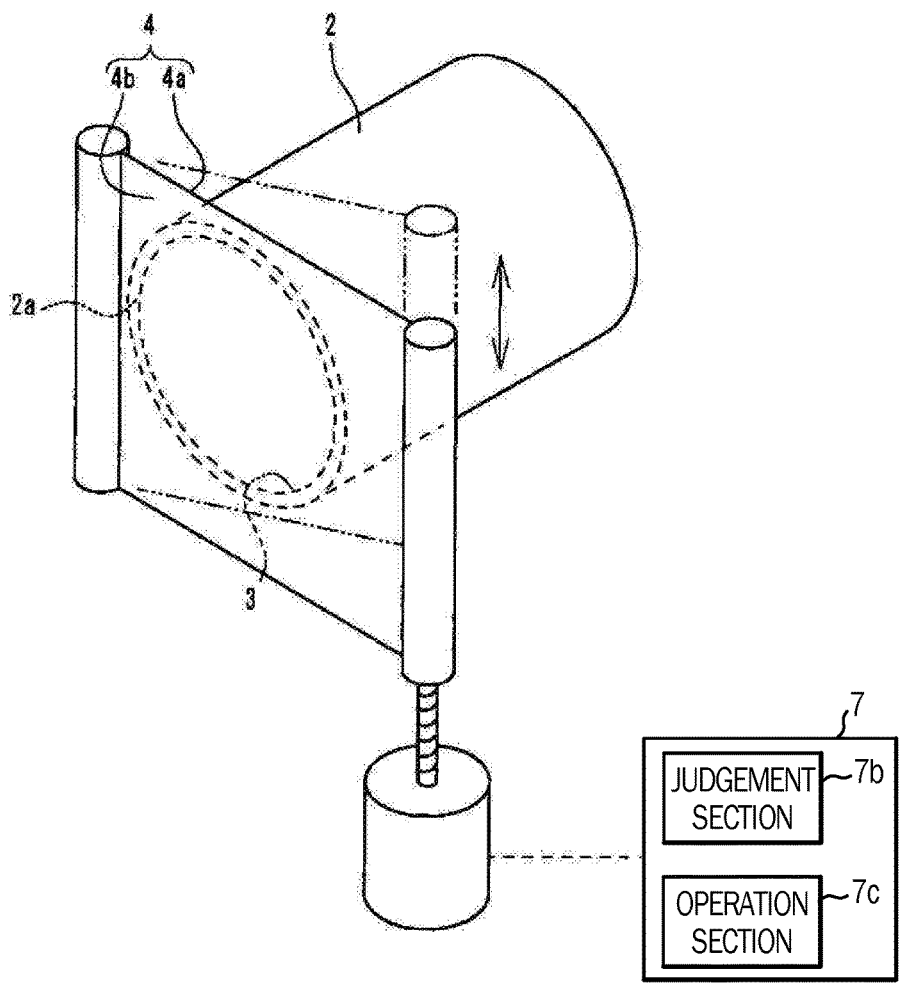
FIG. 17 is a perspective view illustrating a configuration of a concentration meter of a sixth embodiment.

The concentration meter 1 of the present embodiment illustrated in FIG. 17 differs from the first to the third embodiments in the configuration of the adjustment section 10 that applies a mechanical load to the permeation membrane 4 and control by the control section 7. The adjustment section 10 of the present embodiment includes the first holding portion 15, the second holding portion 16 and the actuator 17.

The permeation membrane 4 of the present embodiment is in a rectangular shape. To the respective two parallel sides of the outer shape of the permeation membrane 4, the first holding portion 15 and the second holding portion 16 that are the rectilinear rod-shaped members are fixed. That is, the first holding portion 15 and the second holding portion 16 extend parallel with each other, and the permeation membrane 4 is provided by being stretched between the first holding portion 15 and the second holding portion 16.

A position of the first holding portion 15 is fixed with respect to the housing 2. Further, the second holding portion 16 is movable to advance and retreat with respect to the housing 2. The second holding portion 16 moves to advance and retreat in the direction parallel with the extending direction of the second holding portion 16 on the plane parallel with the surface of the permeation membrane 4. The actuator 17 includes, for example, an electric motor, and a mechanism that converts a rotational motion of the electric motor into a linear motion, and drives the second holding portion 16 in accordance with rotation of the electric motor.

The adjustment section 10 of the present embodiment moves the two parallel sides of outer sides of the permeation membrane 4 which is in a rectangular shape relatively to opposite directions along the respective extending directions by driving the second holding portion 16 by the actuator 17. That is, the adjustment section 10 of the present embodiment can cause the permeation membrane 4 to perform shear deformation on the plane that is parallel with the surface of the permeation membrane 4. In this way, the mechanical load which is applied to the permeation membrane 4 by the adjustment section 10 of the present embodiment is a shearing stress.

When the judgment section 7b judges that the measurement surface 4b of the permeation membrane 4 is in a wet state, the control section 7 of the present embodiment controls the adjustment section 10 to apply a shearing stress to the permeation membrane 4 to cause the permeation membrane 4 to perform shear deformation (a state illustrated by an alternate long and two short dashes line in FIG. 17). Further, when the judgment section 7b judges that the measurement surface 4b of the permeation membrane 4 is in a dry state, the control section 7 cancels the shearing stress that is applied to the permeation membrane 4 and cancels shear deformation (a state illustrated by a solid line in FIG. 17).

The opening shape of the hole 4c of the permeation membrane 4 in a state where the shear deformation is not applied by the adjustment section 10 is a substantially circular shape, for example. The opening shape of the hole 4c of the permeation membrane 4 in a state where the shearing stress is applied by the adjustment section 10 is flatter than the opening shape of the hole 4c of the permeation membrane 4 in the state where the shearing stress is not applied.

Accordingly, in the present embodiment, the width of the opening of the hole 4c is larger in the permeation membrane 4 to which no shearing stress is applied, than in the permeation membrane 4 to which a shearing stress is applied. Accordingly, in the permeation membrane 4 to which no shearing stress is applied, the permeation amount per unit time period of the measurement target in the liquid 20 increases, with respect to the permeation membrane 4 to which a shearing stress is applied.

As described above, the concentration meter 1 of the present embodiment increases the permeation amount per unit time period of the measurement target, of the permeation membrane 4 in the case where the measurement surface 4b is in a dry state as compared with the case where the measurement surface 4b is in a dry state by changing the shearing stress which is applied to the permeation membrane 4.

Accordingly, even when a concentration measurement operation is started in the state where the measurement surface 4b of the permeation membrane 4 is dry, the concentration meter 1 and the endoscope reprocessor including the concentration meter 1 of the present embodiment can cause the measurement target in the liquid 20 that contacts the measurement surface 4b to permeate to the internal liquid 5 side quickly by increasing the tensile force which is applied to the permeation membrane 4, and therefore, can reduce the time period until concentration measurement can be started.

Seventh Embodiment

Next, a seventh embodiment of the present invention will be described. Hereinafter, only difference from the first to the third embodiments will be described, similar components to the components in the first to the third embodiments will be assigned with the same reference signs, and explanation of the similar components will be properly omitted.

Figure 18:
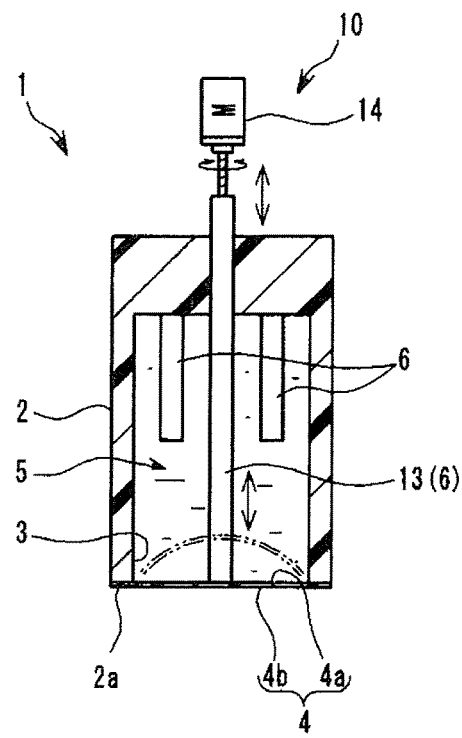
FIG. 18 is a perspective view illustrating a configuration of a concentration meter of a seventh embodiment.

The concentration meter 1 of the present embodiment illustrated in FIG. 18 differs from the first to the third embodiments in the configuration of the adjustment section 10 that applies a mechanical load to the permeation membrane 4 and control by the control section 7.

As illustrated in FIG. 18, the permeation membrane 4 of the present embodiment is provided by being stretched at the distal end portion 2a of the housing 2 in such a manner as to seal the cavity 3.

The adjustment section 10 deforms the measurement surface 4b between a state where the measurement surface 4b of the permeation membrane 4 is substantially flat as illustrated by a solid line in FIG. 18, and a state where the measurement surface 4b is in a shape of a substantially concave surface as illustrated by an alternate long and two short dashes line in FIG. 18.

Although the configuration of the adjustment section 10 is not specially limited, the adjustment section 10 includes the rod 13 that is placed in the cavity 3, and moves to advance and retreat in the direction orthogonal to the releasing surface 4a of the permeation membrane 4, and the actuator 14 that drives the rod 13. The rod 13 extends in the direction orthogonal to the releasing surface 4a of the permeation membrane 4, in the cavity 3. The distal end portion 13a of the rod 13 is fixed to the releasing surface 4a of the permeation membrane 4. The proximal end portion 13b of the rod 13 protrudes to an outside of the housing 2, and is connected to the actuator 14. In the present embodiment, as one example, a part of the rod 13 configures the electrode 6.

The actuator 10b includes, for example, an electric motor, and a mechanism that converts a rotational motion of the electric motor into a linear motion, and drives the rod 13 in the direction orthogonal to the releasing surface 4a in accordance with rotation of the electric motor.

The adjustment section 10 applies a stress that deforms the membrane 4 so that the measurement surface 4b is in the shape of a substantially concave surface by moving the rod 13 to the proximal end side and pulling the permeation membrane 4 to the inside of the cavity 3. The stress which is applied to the permeation membrane 4 by the adjustment section 10 is substantially perpendicular to the surface of the permeation membrane 4.

When the judgment section 7b judges that the measurement surface 4b of the permeation membrane 4 is in a wet state, the control section 7 of the present embodiment deforms the permeation membrane 4 so that the measurement surface 4b is in the shape of a substantially concave surface by controlling the adjustment section 10 to apply the stress perpendicular to the surface of the permeation membrane 4 (the state illustrated by the alternate long and two short dashes line in FIG. 18). Further, when the judgment section 7b judges that the measurement surface 4b of the permeation membrane 4 is in a dry state, the control section 7 controls the adjustment section 10 to cancel the stress which is applied to the permeation membrane 4, and causes the measurement surface 4b to be in a substantially flat shape.

Figure 19:
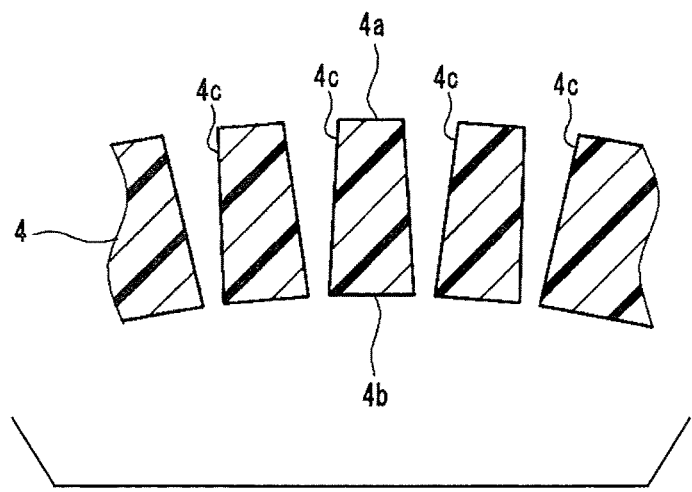
FIG. 19 is a view illustrating a section of a permeation membrane of the seventh embodiment by enlarging the section of the permeation membrane.

As illustrated in FIG. 19, the hole 4c of the permeation membrane 4 in the state where the measurement surface 4b deforms so as to be in the shape of a substantially concave surface has a small opening area at the measurement surface 4b side.

Accordingly, in the present embodiment, in the permeation membrane 4 that deforms so that the measurement surface 4b is in the shape of a substantially concave surface, the opening area of the hole 4c is smaller than in the permeation membrane 4 in which the measurement surface 4b is in a flat shape. Accordingly, in the permeation membrane 4 in which no stress is applied by the adjustment section 10, the permeation amount per unit time period of the measurement target in the liquid 20 increases, with respect to the permeation membrane 4 to which stress is applied.

As described above, the concentration meter 1 of the present embodiment increases the permeation amount per unit time period of the measurement target, of the permeation membrane 4 in the case where the measurement surface 4b is in a dry state as compared with the case where the measurement surface 4b is in a dry state, by changing the stress in the perpendicular direction, which is applied to the permeation membrane 4.

Accordingly, even when a concentration measurement operation is started in the state where the measurement surface 4b of the permeation membrane 4 is dry, the concentration meter 1 and the endoscope reprocessor including the concentration meter 1 of the present embodiment can cause the measurement target in the liquid 20 that contacts the measurement surface 4b to permeate to the internal liquid 5 side quickly by increasing the tensile force which is applied to the permeation membrane 4, and therefore, can reduce the time period until concentration measurement can be started.

Eighth Embodiment

As the adjustment section 10, for example, a structure is cited, in which an electromagnet is disposed in either one of the outer frame 11 and the housing 2, a substance that adsorbs to a magnetic body such as a metal is disposed at the other one, and a spring is disposed between the outer frame 11 and the housing 2. By the structure like this being adopted, the outer frame 11 and the housing 2 are separated by a force of the spring when the electromagnet is not energized, and when the electromagnet is energized, the metal is attracted to the energized electromagnet so that the outer frame 11 and the housing 2 can be moved to close to each other.

(Modification)

In the aforementioned embodiments, in order to keep the modification state of the membrane, the pantograph jacks or the actuators are used, but in place of the pantograph jacks or the actuators, ratchet cam type switches or heart-shaped cam type switches can be used. As means that switches the state of the switch, a solenoid, for example, can be used.

When the switches are used, the advantage that the energized state does not have to be kept to keep the deformation state is provided.

Note that the present invention is not limited to the aforementioned embodiments, but the present invention can be properly changed in the range without departing from the gist or the idea of the invention readable from the claims and the entire description, and the concentration meter and the endoscope reprocessor involving the changes like this are also included in the technical range of the present invention.

According to the present invention, the concentration meter and the endoscope reprocessor that reduces the time period until concentration measurement can be started when the permeation membrane is in a dry state can be provided.

What is claimed is:

1. A concentration meter, comprising:
   a housing having a cavity;
   an electrode accommodated in the cavity;
   a permeation membrane configured to have a measurement surface that contacts a measurement target, a releasing surface configured to release the measurement target that enters from the measurement surface into the cavity, and a plurality of holes configured to open to the measurement surface and the releasing surface, and are for the measurement target to enter, and seals the cavity;
   an internal liquid that is sealed in the cavity, and contacts the electrode and the permeation membrane;
   a main body connection section configured for electrically connecting the electrode to an endoscope reprocessor main body;
   an adjustment section configured to apply a mechanical load to the permeation membrane so that opening areas of the holes in at least the measurement surface reversibly increase or decrease; and
   a control section configured to be connected to the adjustment section, and controls change of strength of the mechanical load that is applied to the permeation membrane, or presence or absence of the mechanical load that is applied to the permeation membrane.

2. The concentration meter according to claim 1, wherein the adjustment section changes a tensile force that is applied to the permeation membrane.

3. The concentration meter according to claim 2, wherein the adjustment section applies the tensile force isotropically to the permeation membrane.

4. The concentration meter according to claim 2, wherein the adjustment section applies the tensile force to the permeation membrane along a single axis.

5. The concentration meter according to claim 2, wherein the adjustment section comprises:
   the housing and
   an outer frame configured to hold the permeation membrane, and extend the permeation membrane and cancel extension by being disposed at an outer circumference of the housing and advancing and retreating along the housing.

6. The concentration meter according to claim 1, wherein the adjustment section deforms the measurement surface having the permeation membrane into a shape of a concave surface or a shape having a convex surface.

7. The concentration meter according to claim 1, wherein the adjustment section applies a shearing stress to the permeation membrane.

8. An endoscope reprocessor, comprising:
   the concentration meter according to claim 1;
   a medicinal solution tank configured to store a medicinal solution including the measurement target;
   a holding portion configured to hold the housing so that the permeation membrane is immersed in the medicinal solution in the medicinal solution tank; and
   an electric contact point configured to be connected to the main body connection section.

* * * * *